(12) United States Patent
Ji et al.

(10) Patent No.: US 11,260,010 B2
(45) Date of Patent: Mar. 1, 2022

(54) COCHELATES USING PHOSPHATIDYLSERINE/ANIONIC SURFACTANT/CALCIUM CHLORIDE

(71) Applicant: H&A PHARMACHEM CO., LTD, Gyeonggi-do (KR)

(72) Inventors: Hong Geun Ji, Gyeonggi-do (KR); Hae In Choi, Incheon (KR); Young Ah Park, Incheon (KR); Yu Jin Kang, Gyeonggi-do (KR)

(73) Assignee: H&A PHARMACHEM CO., LTD, Gyeonggi-Do (KR)

( * ) Notice: Subject to any disclaimer, the term of this patent is extended or adjusted under 35 U.S.C. 154(b) by 3 days.

(21) Appl. No.: 16/765,096

(22) PCT Filed: Nov. 26, 2018

(86) PCT No.: PCT/KR2018/014614
§ 371 (c)(1),
(2) Date: May 18, 2020

(87) PCT Pub. No.: WO2019/107849
PCT Pub. Date: Jun. 6, 2019

(65) Prior Publication Data
US 2020/0352841 A1 Nov. 12, 2020

(30) Foreign Application Priority Data
Nov. 30, 2017 (KR) .................. 10-2017-0162564

(51) Int. Cl.
*A61K 8/55* (2006.01)
*A61K 8/20* (2006.01)
(Continued)

(52) U.S. Cl.
CPC ............. *A61K 8/553* (2013.01); *A61K 8/20* (2013.01); *A61K 8/34* (2013.01); *A61K 8/342* (2013.01);
(Continued)

(58) Field of Classification Search
None
See application file for complete search history.

(56) References Cited

U.S. PATENT DOCUMENTS

| 5,643,574 A | 7/1997 | Gould-Fogerite et al. |
| 6,153,217 A | 11/2000 | Jin et al. |

(Continued)

FOREIGN PATENT DOCUMENTS

| JP | 2003-529557 A | 10/2003 |
| JP | 2014-513135 A | 5/2014 |

(Continued)

OTHER PUBLICATIONS

Lee et al., "Effect of surfactant mixtures on irritant contact dermatitis potential in man: sodium lauroyl glutamate and sodium lauryl sulphate", Clinical Trial, Contact Dermatitis, Apr. 1994; 30(4):205-9. (Year: 1994).*

(Continued)

*Primary Examiner* — Kyung S Chang
(74) *Attorney, Agent, or Firm* — Harness, Dickey & Pierce, P.L.C.

(57) ABSTRACT

The present invention relates to cochleates using phosphatidylserine/anionic surfactant/calcium chloride and, more specifically, to cochleates comprising phosphatidylserine, an anionic surfactant, calcium chloride, an active ingredient, and water.

20 Claims, 6 Drawing Sheets

(51) Int. Cl.
| | |
|---|---|
| *A61K 8/34* | (2006.01) |
| *A61K 8/365* | (2006.01) |
| *A61K 8/42* | (2006.01) |
| *A61K 8/44* | (2006.01) |
| *A61K 8/49* | (2006.01) |
| *A61K 8/63* | (2006.01) |
| *A61K 8/9794* | (2017.01) |
| *A61K 8/9789* | (2017.01) |
| *A61K 8/64* | (2006.01) |
| *A61K 8/67* | (2006.01) |
| *A61K 8/73* | (2006.01) |
| *A61Q 7/00* | (2006.01) |
| *A61Q 17/04* | (2006.01) |
| *A61Q 19/00* | (2006.01) |
| *A61Q 19/02* | (2006.01) |
| *A61Q 19/08* | (2006.01) |

(52) U.S. Cl.
CPC ............ *A61K 8/365* (2013.01); *A61K 8/42* (2013.01); *A61K 8/44* (2013.01); *A61K 8/4913* (2013.01); *A61K 8/63* (2013.01); *A61K 8/64* (2013.01); *A61K 8/671* (2013.01); *A61K 8/673* (2013.01); *A61K 8/675* (2013.01); *A61K 8/676* (2013.01); *A61K 8/678* (2013.01); *A61K 8/735* (2013.01); *A61K 8/9789* (2017.08); *A61K 8/9794* (2017.08); *A61Q 7/00* (2013.01); *A61Q 17/04* (2013.01); *A61Q 19/007* (2013.01); *A61Q 19/02* (2013.01); *A61Q 19/08* (2013.01)

(56) References Cited

U.S. PATENT DOCUMENTS

2004/0185057 A1\* 9/2004 Kirkby .................. A61P 35/00
  424/185.1
2014/0220108 A1 8/2014 Lu et al.

FOREIGN PATENT DOCUMENTS

| JP | 2016-222612 A | 12/2016 |
|---|---|---|
| KR | 10-2015-0107707 A | 9/2015 |
| WO | WO-1996-025942 A1 | 8/1996 |
| WO | WO-2014-022414 A1 | 2/2014 |

OTHER PUBLICATIONS

International Search Report issued in International Patent Application No. PCT/KR2018/014614, dated May 10, 2019, with English Translation.

\* cited by examiner

COCHELATES USING PHOSPHATIDYLSERINE/ANIONIC SURFACTANT/CALCIUM CHLORIDE

CROSS-REFERENCE TO RELATED APPLICATIONS

This application is a national phase application of PCT Application No. PCT/KR2018/014614, filed on Nov. 26, 2018, which claims priority to Korean Patent Application No. 10-2017-0162564, filed on Nov. 30, 2017. The entire disclosure of the applications identified in this paragraph is incorporated herein by reference.

FIELD

The present invention relates to a cochleate using phosphatidylserine/anionic surfactant/calcium chloride. More specifically, the present invention relates to a cochleate comprising phosphatidylserine, anionic surfactant, calcium chloride, an active ingredient and water.

BACKGROUND

To stabilize an active ingredient and increase transdermal efficiency, efforts and study for utilizing a transdermal delivery system to functional cosmetics have been actively carried out. Such transdermal delivery systems are mainly used to make and apply vesicles containing active ingredients from materials such as surfactants, lipids and polymers. Of these materials, lipids have advantages due to components of the biomembrane, so they are widely used as cosmetic materials.

One of the delivery systems using lipids that has attracted attention is cochleate technology. Cochleate technology was developed for the therapeutic oral delivery of hydrophobic drugs, and a negatively charged phospholipid bilayer and poly-cationic metal ions form a spiral structure. In the early stages of development of cochleates, unlike liposomes, they had an internal structure without water, but recently structures containing water have also been developed.

Cochleate technology was developed in the mid-1970s and has been used for drug delivery. Cochleates have received a great deal of attention in drug delivery due to their potential for oral use and improved stability. Cochleates are formed by ion interaction of a bilayer of liposome composed of phospholipids and cation, and forms an elongated shape like a spiral cylinder in order to minimize the interaction between them (FIG. 1). Cochleates are stable in freeze-drying and can stably encapsulate drugs or peptides in a phospholipid bilayer to protect them from external environments (e.g., osmotic phenomena, pH, enzymes, temperature conditions, etc.). Cochleates are expected to serve as an excellent delivery system for cosmetic ingredients due to their unique characteristics with a spiral rod shape and a rigid structure.

SUMMARY

Technical Problem

Therefore, the technical problem of the present invention is the provision of a cochleate using phosphatidylserine/anionic surfactant/calcium chloride as a new delivery system which can efficiently deliver an active ingredient in a stable manner.

Solution to Problem

To solve the above technical problem, the present invention provides a cochleate comprising 0.1 to 20% by weight of phosphatidylserine, 0.001 to 5% by weight of anionic surfactant, 0.0001 to 2% by weight of calcium chloride, 0.0005 to 50% by weight of an active ingredient and 30 to 96% by weight of water.

The present invention is described in detail hereinafter.

According to the present invention, there is provided a cochleate comprising 0.1 to 20% by weight of phosphatidylserine, 0.001 to 5% by weight of anionic surfactant, 0.0001 to 2% by weight of calcium chloride, 0.0005 to 50% by weight of an active ingredient and 30 to 96% by weight of water.

The cochleate according to the present invention comprises phosphatidylserine in an amount of 0.1 to 20% by weight, preferably 0.5 to 18% by weight and more preferably 1 to 15% by weight.

Phosphatidylserine is a phospholipid that is a component of the cell membrane, where two fatty acids are ester-linked to the first and second carbon atoms of glycerol, and serine is linked to the third carbon atom of glycerol through a phosphodiester bond. Phosphatidylserine can be extracted in a variety of methods, but can preferably be prepared from lecithin extracted from soybeans. In the cochleate according to the present invention, the phosphatidylserine forms a phospholipid bilayer. In the present invention, if the phosphatidylserine is comprised in an amount of less than 0.1% by weight or more than 20% by weight, there may be a problem in the formation of cochleate.

The cochleate according to the present invention comprises an anionic surfactant in an amount of 0.001 to 5% by weight, preferably 0.01 to 3% by weight and more preferably 0.1 to 2% by weight.

In the present invention, the anionic surfactant may be preferably selected from sodium stearoyl glutamate, disodium stearoyl glutamate, sodium lauroyl glutamate, sodium lauroyl glutamate, sodium lauryl glucose carboxylate glucose carboxylate and sodium methyl cocoyl taurate, and may be most preferably sodium stearoyl glutamate.

In the present invention, the anionic surfactant can help in the formation of liposome formed by the bilayer of phosphatidylserine as a pre-step for forming a cochleate, so that a stable cochleate can be formed. In the present invention, if the anionic surfactant is comprised in an amount of less than 0.001% by weight or more than 5% by weight, there may be a problem in the formation of cochleate.

The cochleate according to the present invention comprises calcium chloride in an amount of 0.0001 to 2% by weight, preferably 0.0005 to 1.8% by weight and more preferably 0.001 to 1.5% by weight.

In the present invention, calcium ions of calcium chloride form a cochleate by ion interaction with the bilayers of phosphatidylserine, and serve as a bridge between the bilayers of phosphatidylserine. In the present invention, if the calcium chloride is comprised in an amount of less than 0.0001% by weight or more than 2% by weight, there may be a problem in the formation of cochleate.

The cochleate according to the present invention comprises an active ingredient in an amount of 0.0005 to 50% by weight, preferably 0.001 to 45% by weight and more preferably 0.002 to 40% by weight. In the present invention, if the amount of the active ingredient is less than 0.0005% by weight, the efficacy according to an active ingredient may be weak, and if the amount of the active ingredient is more than 50% by weight, there may be a problem in the formation of cochleate.

In the present invention, there is no special limitation according to an active ingredient. In the present invention, examples of an active ingredient include, but are not limited to, one or more selected from a moisturizer, a whitening agent, an anti-wrinkle agent, a UV blocking agent, a hair growth promoter, vitamin or a derivative thereof, amino acid or peptide, an anti-inflammatory agent, an acne therapeutic agent, a microbicide, female hormone, a keratolytic agent and a natural product. In addition, cosmetic ingredients such as oils, waxes, butters, paraffin, higher fatty acids such as stearic acid, esters such as cetyl ethylhexanoate, and silicones may also be used as an active ingredient.

Examples of moisturizer include, but are not limited to, creatine, polyglutamic acid, sodium lactate, hydroproline, 2-pyrrolidone-5-carboxyclic acid sodium salt, hyaluronic acid, sodium hyaluronate, ceramide, phytosteryl, cholesterol, sitosterol, pullulan and proteoglycan. Examples of whitening agent include, but are not limited to, arbutin and a derivative thereof, kojic acid, bisabolol, niacinamide, vitamin C and a derivative thereof, placenta and allantoin. Examples of anti-wrinkle agent include, but are not limited to, retinol, retinol derivative, adenosine, licorice extract, red *Ginseng* extract and *Ginseng* extract. Examples of UV blocking agent include, but are not limited to, benzophenone derivative, para-aminobenzoic acid derivative, methoxycinnamic acid derivative and salicylic acid derivative. There is no special limitation to a hair growth promoter, but it may be preferably a blood circulation promoter and/or a hair follicle stimulant. Examples of blood circulation promoter include, but are not limited to, the extract of *Swertia japonica* Makino, cepharanthin, vitamin E and a derivative thereof and gamma-oryzanol, and examples of hair follicle stimulant include, but are not limited to, *Capsicum* tincture, ginger tincture, cantharides tincture and nicotinic acid benzyl ester. Examples of vitamin or a derivative thereof include, but are not limited to, vitamin A (retinol) and a derivative thereof, vitamin B1, vitamin B2, vitamin B6, vitamin E and derivatives thereof, vitamin D, vitamin H, vitamin K, pantothenic acid and derivatives thereof, biotin, panthenol, coenzyme $Q_{10}$ and idebenone. Examples of amino acid or peptide include, but are not limited to, cysteine, methionine, serine, lysine, tryptophan, amino acid extract, epidermal growth factor (EGF), insulin-like growth factor (IGF), fibroblast growth factor (FGF), copper tripeptide-1, tripeptide-29, tripeptide-1, acetyl hexapeptide-8, nicotinoyl tripeptide-35, hexapeptide-12, hexapeptide-9, palmitoyl pentapeptide-4, palmitoyl tetrapeptide-7, palmitoyl tripeptide-29, palmitoyl tripeptide-1, nonapeptide-7, tripeptide-10 citrulline, sh-polypeptide-15, palmitoyl tripeptide-5, diaminopropionoyl tripeptide-33 and r-spider polypeptide-1. Examples of anti-inflammatory agent include, but are not limited to, beta-glycyrrhetinic acid, glycyrrhetinic acid derivative, aminocaproic acid, hydrocortisone, 3-glucan and licorice. Examples of acne therapeutic agent include, but are not limited to, estradiol, estrogen, ethinyl estradiol, triclosan and azelaic acid. Examples of microbicide include, but are not limited to, benzalkonium chloride, benzethonium chloride and halocalban. There is no special limitation to female hormone, but it may be preferably estrogen. As estrogen, it may be preferably estradiol, ethinyl estradiol or isoflavone which is a phytoestrogen. Examples of keratolytic agent include, but are not limited to, sulfur, salicylic acid, AHA, BHA and resorcin. Examples of the extract of natural product or an ingredient obtained therefrom include, but are not limited to, the extract of Japanese witch-hazel, *Lamium album* var. *barbatum*, *Hedyotis diffusa*, *Rheum palmatum*, licorice, aloe, chamomile, rose hip, horse chestnut, *Ginseng*, *Luffa aegyptiaca*, cucumber, laver, sea mustard, *Dioscorea batatas*, snail and fruit of *Dioscorea polystachya*, or hinokitiol and beta-carotene. In addition, yeast extract, collagen, elastin, DHA, EPA, flavor ingredient and the like may be used.

The cochleate according to the present invention comprises water in an amount of 30 to 96% by weight, preferably 40 to 95% by weight and more preferably 50 to 94% by weight.

The cochleate according to the present invention may further comprise an additive (e.g., an antioxidant), if necessary.

Effects of the Invention

A cochleate according to the present invention can show excellent efficacy even with a small amount of an active ingredient by increasing bioavailability in which an active ingredient is efficiently transferred in a very stable form within a firm structure.

DETAILED DESCRIPTION

Figure 1:
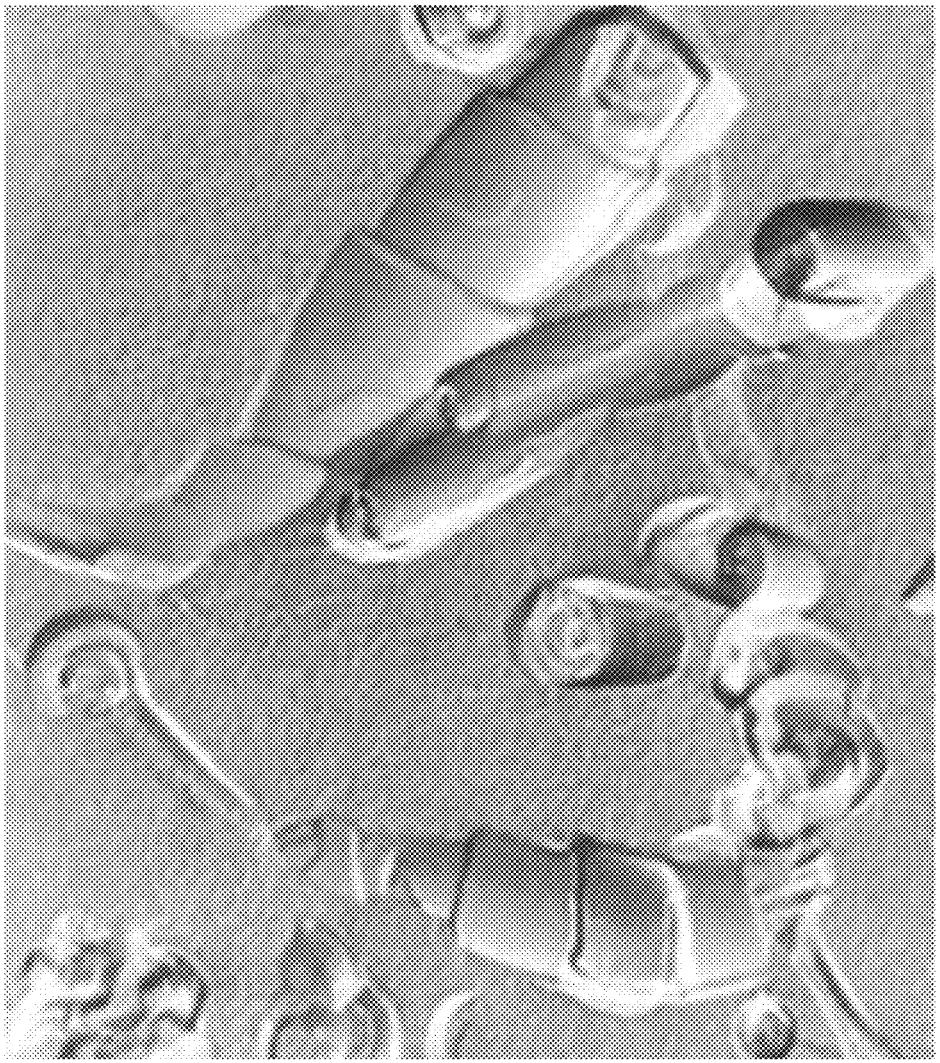
FIG. 1 is an electron microscopy photograph of cochleate.
Figure 2:
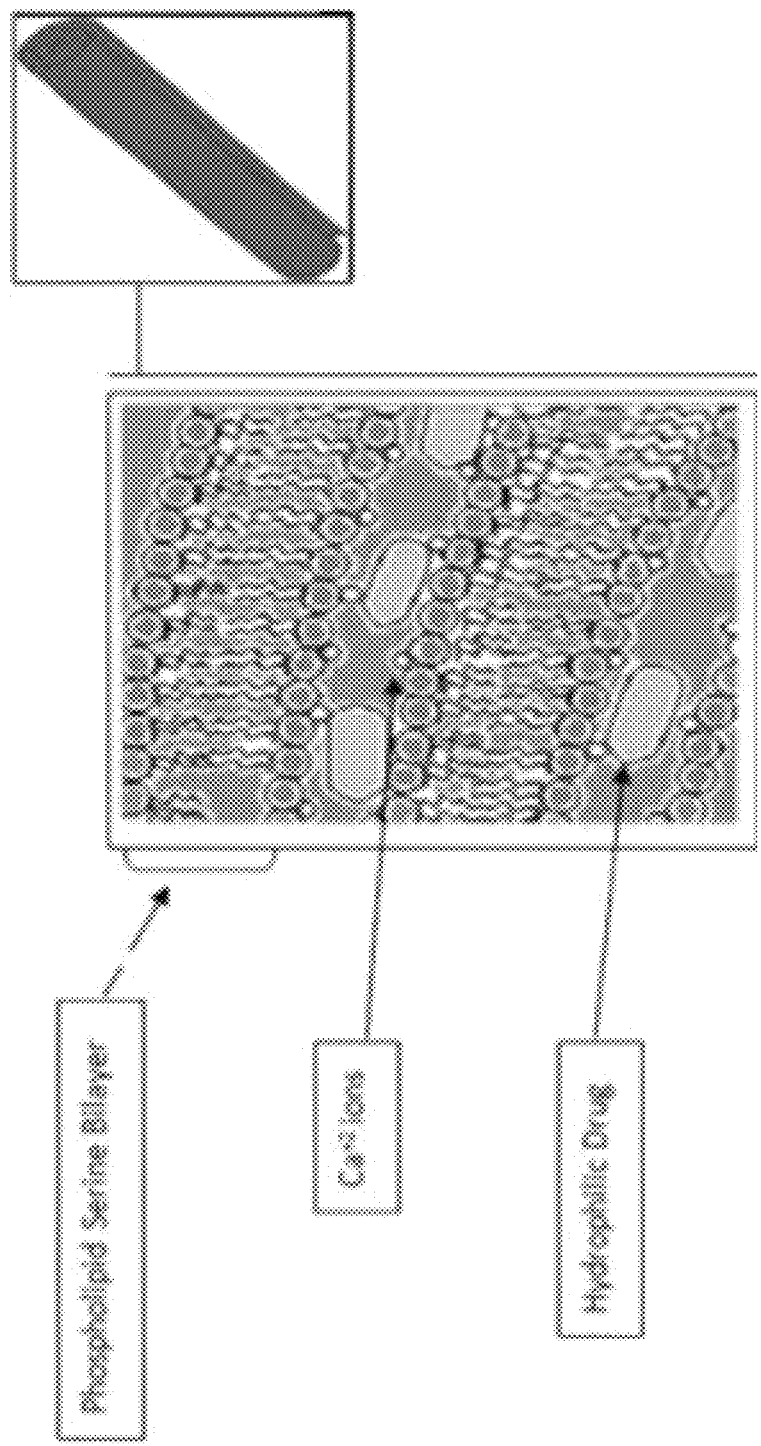
FIG. 2 is a schematic diagram representing the structure of cochleate.

Hereinafter, the present invention is explained in more detail with the following examples. However, it must be understood that the protection scope of the present invention is not limited to the examples.

Examples 1 to 18: Preparation of Cochleate Containing Various Active Ingredients According to the constitutional compositions of Tables 1 to 18, cochleates were prepared by continuously passing the ingredients five (5) times through a high-pressure microfluidizer at 1,000 bar.

Example 1: Preparation of Cochleate Containing Plant Natural Product

TABLE 1

| Ingredient | Content (% by weight) |
| --- | --- |
| Phosphatidylserine | 3 |
| Sodium stearoyl glutamate | 0.5 |
| Calcium chloride | 0.1 |
| *Ginkgo* leaf extract | 20 |
| Distilled water | 76.4 |
| Total amount | 100 |

Example 2: Preparation of Cochleate Containing Marine Natural Product

TABLE 2

| Ingredient | Content (% by weight) |
| --- | --- |
| Phosphatidylserine | 3 |
| Sodium stearoyl glutamate | 0.5 |
| Calcium chloride | 0.1 |
| Kelp extract | 10 |
| Distilled water | 86.4 |
| Total amount | 100 |

Example 3: Preparation of Cochleate Containing Oil

TABLE 3

| Ingredient | Content (% by weight) |
| --- | --- |
| Phosphatidylserine | 5 |
| Sodium stearoyl glutamate | 0.6 |
| Calcium chloride | 0.05 |
| Olive oil | 20 |
| *Camellia* oil | 2 |
| *Macadamia* nut oil | 2 |
| Castor oil | 2 |
| Sunflower oil | 2 |
| Jojoba oil | 2 |
| Almond oil | 2 |
| Apricot seed oil | 2 |
| Green tea oil | 2 |
| Meadowfoam seed oil | 2 |
| Argan oil | 2 |
| Distilled water | 72.35 |
| Total amount | 100 |

Example 4: Preparation of Cochleate Containing Wax

TABLE 4

| Ingredient | Content (% by weight) |
| --- | --- |
| Phosphatidylserine | 2 |
| Sodium stearoyl glutamate | 0.1 |
| Calcium chloride | 0.05 |
| Beeswax | 5 |
| Candelilla wax | 5 |
| Distilled water | 87.85 |
| Total amount | 100 |

Example 5: Preparation of Cochleate Containing Butter

TABLE 5

| Ingredient | Content (% by weight) |
| --- | --- |
| Phosphatidylserine | 6 |
| Sodium stearoyl glutamate | 0.8 |
| Calcium chloride | 0.001 |
| Shea butter | 5 |
| Mango butter | 5 |
| Green tea butter | 5 |
| Distilled water | 78.199 |
| Total amount | 100 |

Example 6: Preparation of Cochleate Containing Paraffin

TABLE 6

| Ingredient | Content (% by weight) |
| --- | --- |
| Phosphatidylserine | 3 |
| Sodium stearoyl glutamate | 0.5 |
| Calcium chloride | 0.1 |
| Paraffin | 20 |
| Distilled water | 76.4 |
| Total amount | 100 |

Example 7: Preparation of Cochleate Containing Higher Fatty Acid

TABLE 7

| Ingredient | Content (% by weight) |
| --- | --- |
| Phosphatidylserine | 1 |
| Sodium stearoyl glutamate | 0.1 |
| Calcium chloride | 0.1 |
| Stearic acid | 6 |
| Distilled water | 92.8 |
| Total amount | 100 |

Example 8: Preparation of Cochleate Containing Ester

TABLE 8

| Ingredient | Content (% by weight) |
| --- | --- |
| Phosphatidylserine | 8 |
| Sodium stearoyl glutamate | 0.9 |
| Calcium chloride | 0.5 |
| Cetyl ethylhexanoate | 20 |
| Distilled water | 70.6 |
| Total amount | 100 |

Example 9: Preparation of Cochleate Containing Silicone

TABLE 9

| Ingredient | Content (% by weight) |
| --- | --- |
| Phosphatidylserine | 6 |
| Sodium stearoyl glutamate | 0.1 |
| Calcium chloride | 0.4 |

TABLE 9-continued

| Ingredient | Content (% by weight) |
| --- | --- |
| Dimethicone | 30 |
| Distilled water | 63.5 |
| Total amount | 100 |

Example 10: Preparation of Cochleate Containing Moisturizer

TABLE 10

| Ingredient | Content (% by weight) |
| --- | --- |
| Phosphatidylserine | 5 |
| Sodium stearoyl glutamate | 0.5 |
| Calcium chloride | 0.1 |
| Ceramide | 5 |
| Hyaluronic acid | 0.5 |
| Polyglutamic acid | 0.1 |
| Proteoglycan | 0.0001 |
| Distilled water | 88.7999 |
| Total amount | 100 |

Example 11: Preparation of Cochleate Containing Whitening Agent

TABLE 11

| Ingredient | Content (% by weight) |
| --- | --- |
| Phosphatidylserine | 6 |
| Sodium stearoyl glutamate | 0.7 |
| Calcium chloride | 1 |
| Arbutin | 20 |
| Distilled water | 72.3 |
| Total amount | 100 |

Example 12: Preparation of Cochleate Containing UV Blocking Agent

TABLE 12

| Ingredient | Content (% by weight) |
| --- | --- |
| Phosphatidylserine | 8 |
| Sodium stearoyl glutamate | 1 |
| Calcium chloride | 0.15 |
| Octyl methoxycinnamate | 20 |
| Distilled water | 70.85 |
| Total amount | 100 |

Example 13: Preparation of Cochleate Containing Vitamin

TABLE 13

| Ingredient | Content (% by weight) |
| --- | --- |
| Phosphatidylserine | 5 |
| Sodium stearoyl glutamate | 0.8 |
| Calcium chloride | 0.5 |
| *Macadamia* nut oil | 10 |
| Vitamin A (retinol) | 5 |
| Distilled water | 78.7 |
| Total amount | 100 |

Example 14: Preparation of Cochleate Containing Amino Acid and Peptide

TABLE 14

| Ingredient | Content (% by weight) |
| --- | --- |
| Phosphatidylserine | 5 |
| Sodium stearoyl glutamate | 0.7 |
| Calcium chloride | 0.3 |
| Cysteine | 10 |
| Epidermal growth factor (EGF) | 0.0001 |
| Insulin-like growth factor (IGF) | 0.001 |
| Distilled water | 83.9989 |
| Total amount | 100 |

Example 15: Preparation of Cochleate Containing Peptide

TABLE 15

| Ingredient | Content (% by weight) |
| --- | --- |
| Phosphatidylserine | 5 |
| Sodium stearoyl glutamate | 0.7 |
| Calcium chloride | 0.3 |
| Palmitoyl pentapeptide-3 | 0.0001 |
| Hexapeptide-9 | 0.001 |
| Palmitoyl tetrapeptide-7 | 0.00001 |
| Nonapeptide-7 | 0.0001 |
| Dipeptide-8 | 0.001 |
| Distilled water | 93.99779 |
| Total amount | 100 |

Example 16: Preparation of Cochleate Containing Anti-Inflammatory Agent

TABLE 16

| Ingredient | Content (% by weight) |
| --- | --- |
| Phosphatidylserine | 8 |
| Sodium stearoyl glutamate | 0.5 |
| Calcium chloride | 0.3 |
| Hydrocortisone | 5 |
| Distilled water | 86.2 |
| Total amount | 100 |

Example 17: Preparation of Cochleate Containing Acne Therapeutic Agent

TABLE 17

| Ingredient | Content (% by weight) |
| --- | --- |
| Phosphatidylserine | 3 |
| Sodium stearoyl glutamate | 0.7 |
| Calcium chloride | 0.3 |
| Azelaic acid | 20 |
| Distilled water | 76 |
| Total amount | 100 |

Example 18: Preparation of Cochleate Containing Microbicide

TABLE 18

| Ingredient | Content (% by weight) |
| --- | --- |
| Phosphatidylserine | 10 |
| Sodium stearoyl glutamate | 0.7 |
| Calcium chloride | 0.5 |
| Halocalban | 30 |
| Distilled water | 58.8 |
| Total amount | 100 |

Comparative Example: Preparation of General Liposome Containing Retinol

According to the constitutional composition of Table 19, the ingredients were introduced into a vessel. The resulting mixture was continuously passed five (5) times through a high-pressure microfluidizer at 1,000 bar, followed by cooling and deaeration to obtain liposome.

TABLE 19

| Ingredient | Content (% by weight) |
| --- | --- |
| Saturated lecithin | 3 |
| Sodium stearoyl glutamate | 0.8 |
| *Macadamia* nut oil | 10 |
| Retinol | 5 |
| Distilled water | 81.2 |
| Total amount | 100 |

Experimental Example 1: Measurement of Particle Size Distribution

Figure 3:
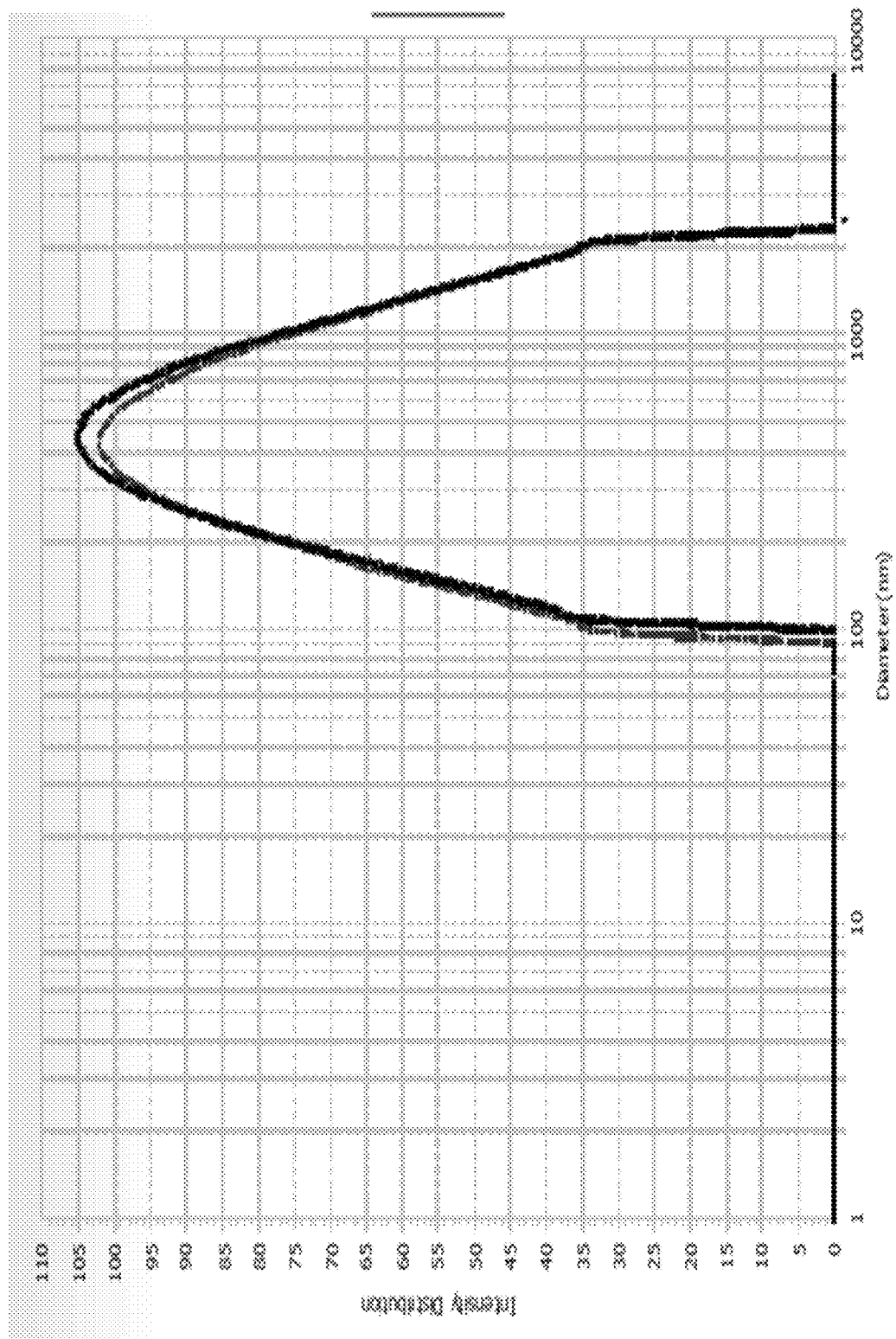
FIG. 3 is a result of measuring the diameter of cochleate by the use of Photal ELS-Z.

The particle size distribution of the cochleates prepared in Example 2 was measured by the use of Photal ELS-Z, and the result is represented in FIG. 3. From the result of the measurement, it can be known that the average particle size of the cochleates is 359.3 nm.

Experimental Example 2: Cryo-Electron Microscopy

Figure 4:
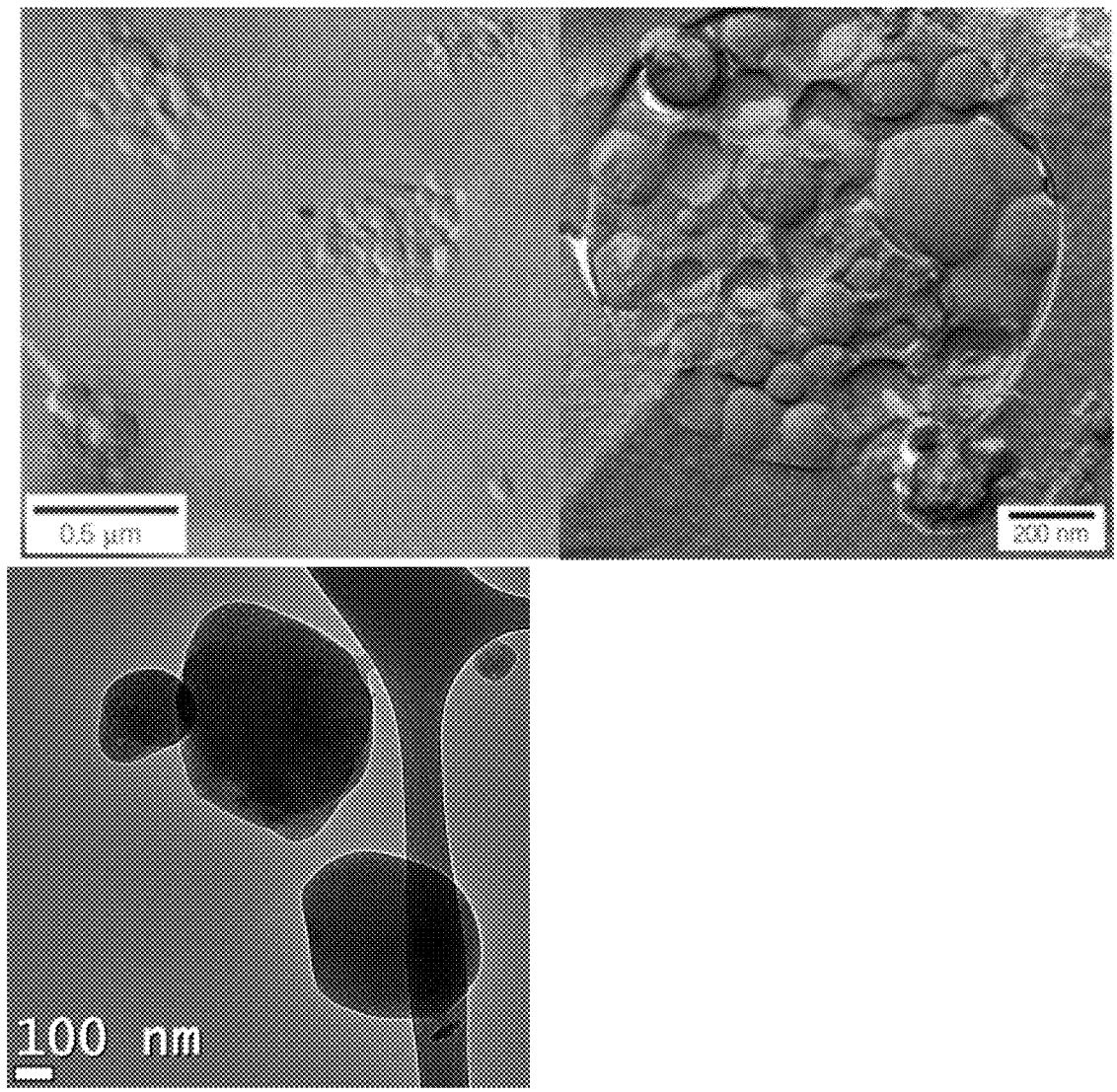
FIG. 4 is a cryo-electron microscopy photograph of particles of cochleates.

Photographs of the cochleates prepared in Example 2 were taken. Due to very fine particle size, it was impossible to take photographs by a general optical microscope. Therefore, cryo-electron microscopy photographs (JEM 1010, JEOL Ltd., Japan) were taken (FIG. 4). From FIG. 4, it can be known that the cochleates are well formed.

Experimental Example 3: Measurement of Stability of Cochleate

Figure 5:
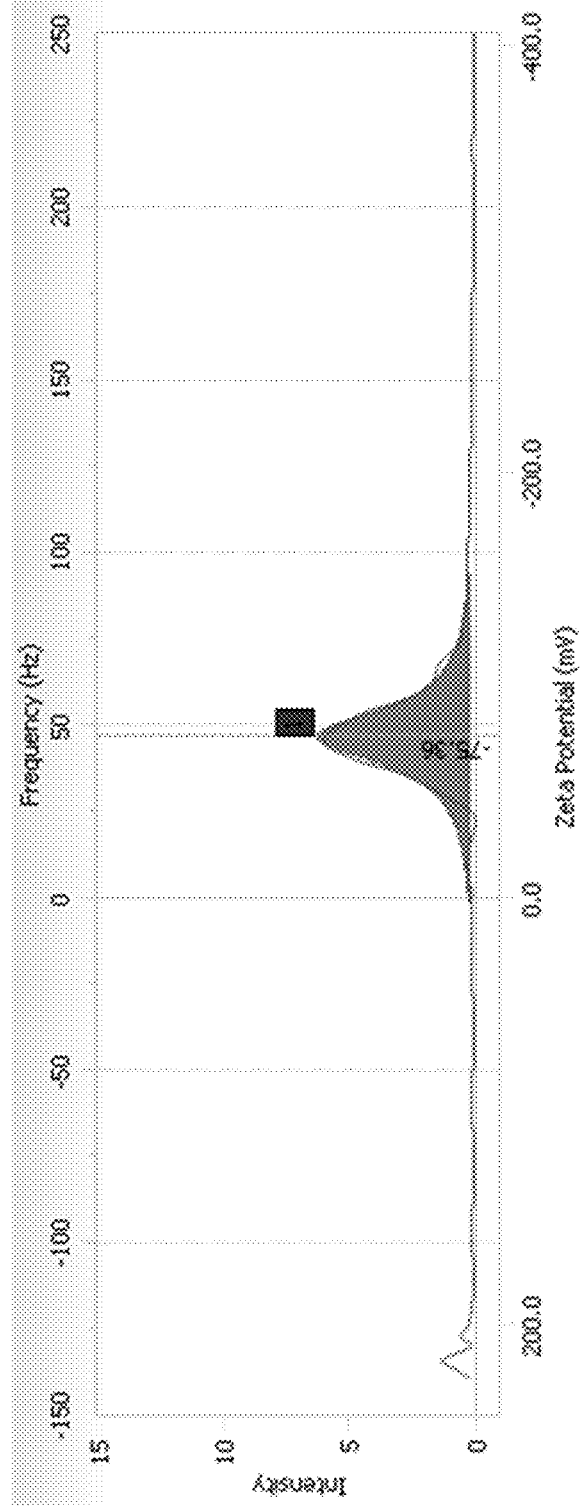
FIG. 5 is a result of measuring zeta potential by the use of Photal ELS-Z to measure the stability of cochleate.

To measure the stability of the cochleates prepared in Example 2, zeta potential was measured by the use of Photal ELS-Z. From the result of the measurement, it can be known that the potential of particle is −75.36 mV, and the cochleates are stable (FIG. 5).

Experimental Example 4: Measurement of Stability of Cochleate

Figure 6:
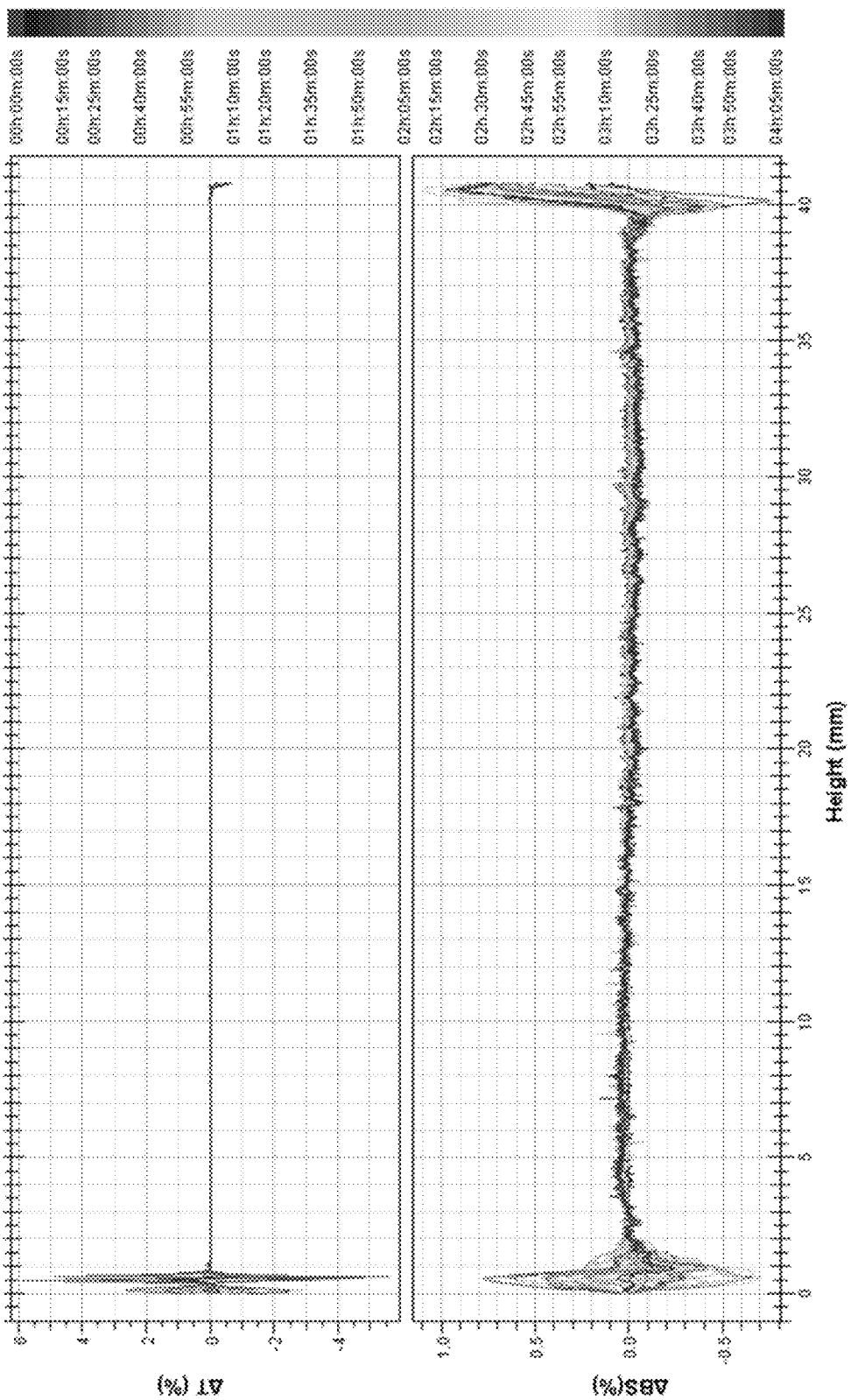
FIG. 6 is a result of measuring the stability of cochleate by the use of Turbiscan.

The stability of the cochleates prepared in Example 2 was measured by the use of Turbiscan. As a result, the stability of the cochleates was confirmed (FIG. 6).

Experimental Example 5: Test for Promoting Transdermal Absorption

The artificial skin, Neoderm (Tego Science, Korea) was mounted to a Franz-type diffusion cell (Lab Fine Instruments, Korea). 50 mM phosphate buffer (pH 7.4, 0.1M NaCl) was added to a receptor cell (5 ml) of the Franz-type diffusion cell. A diffusion cell was then mixed and diffused at 600 rpm, 32° C., and 50 µl of the cochleate containing retinol prepared in Example 13 and the liposome of the Comparative Example, respectively, were added to donor cells. Absorption and diffusion were carried out according to the predetermined time, and the area of the skin where the absorption and diffusion were carried out was 0.64 cm². After finishing the absorption and diffusion of the active ingredient, the residues-which were not absorbed and remained on the skin-were cleaned with dried Kimwipes™ or 10 ml of ethanol. The skin in which the active ingredient was absorbed and diffused was homogenized by the use of a tip-type homogenizer, and retinol absorbed into the skin was then extracted with 4 ml of dichloromethane. The extract was then filtrated with a 0.45 µm nylon membrane filter. The content was measured by high-performance liquid chromatography with the following conditions, and the results are represented in Table 20.

TABLE 20

| | Transdermal absorption (µg) | Rate of increase |
| --- | --- | --- |
| Cochleate of Example 13 | 0.3888 | 16.82% |
| Liposome of Comparative Example | 0.2312 | — |

A) Column: C18 (4.6 × 200 mm, 5 µm)
B) Mobile phase: methanol:hexane = 2:1
C) Flow rate: 0.8 ml/min
D) Detector: UV 275 nm

What is claimed is:

1. A cochleate consisting essentially of 0.1 to 20% by weight of phosphatidylserine, 0.001 to 5% by weight of anionic surfactant, 0.0001 to 2% by weight of calcium chloride, 0.0005 to 50% by weight of an active ingredient and 30 to 96% by weight of water,
wherein the anionic surfactant is selected from the group consisting of sodium stearoyl glutamate, disodium stearoyl glutamate, sodium lauryl glucose carboxylate and sodium methyl cocoyl taurate, and wherein the cochleate does not contain a lipid other than phosphatidylserine.

2. The cochleate according to claim 1, which consists essentially of 0.5 to 18% by weight of phosphatidylserine, 0.01 to 3% by weight of anionic surfactant, 0.0005 to 1.8% by weight of calcium chloride, 0.001 to 45% by weight of the active ingredient and 40 to 95% by weight of water.

3. The cochleate according to claim 2, which consists essentially of 1 to 15% by weight of phosphatidylserine, 0.1 to 2% by weight of anionic surfactant, 0.001 to 1.5% by weight of calcium chloride, 0.002 to 40% by weight of the active ingredient and 50 to 94% by weight of water.

4. The cochleate according to claim 1, wherein the anionic surfactant is sodium stearoyl glutamate.

5. The cochleate according to claim 1, wherein the active ingredient is one or more selected from the group consisting of a moisturizer, a whitening agent, an anti-wrinkle agent, a UV blocking agent, a hair growth promoter, vitamin or a derivative thereof, amino acid or peptide, an anti-inflammatory agent, an acne therapeutic agent, a microbicide, female hormone, a keratolytic agent and a natural product.

6. The cochleate according to claim 5, wherein the moisturizer is one or more selected from the group consisting of creatine, polyglutamic acid, sodium lactate, hydroproline, 2-pyrrolidone-5-carboxyclic acid sodium salt, hyaluronic acid, sodium hyaluronate, ceramide, phytosteryl, cholesterol, sitosterol, pullulan and proteoglycan.

7. The cochleate according to claim 5, wherein the whitening agent is one or more selected from the group consisting of arbutin and a derivative thereof, kojic acid, bisabolol, niacinamide, vitamin C and a derivative thereof, placenta and allantoin.

8. The cochleate according to claim 5, wherein the anti-wrinkle agent is one or more selected from the group consisting of retinol, a retinol derivative, adenosine, licorice extract, red *ginseng* extract and *ginseng* extract.

9. The cochleate according to claim 5, wherein the UV blocking agent is one or more selected from the group consisting of benzophenone derivative, para-aminobenzoic acid derivative, methoxycinnamic acid derivative and salicylic acid derivative.

10. The cochleate according to claim 5, wherein the hair growth promoter is a blood circulation promoter or a hair follicle stimulant.

11. The cochleate according to claim 10, wherein the blood circulation promoter is one or more selected from the group consisting of an extract of *Swertia japonica* Makino, cepharanthin, vitamin E and a derivative thereof, and gamma-oryzanol.

12. The cochleate according to claim 10, wherein the hair follicle stimulant is one or more selected from the group consisting of *capsicum* tincture, ginger tincture, cantharides tincture and nicotinic acid benzyl ester.

13. The cochleate according to claim 5, wherein the vitamin or a derivative thereof is one or more selected from the group consisting of vitamin A and a derivative thereof, vitamin B1, vitamin B2, vitamin B6, vitamin E and derivatives thereof, vitamin D, vitamin H, vitamin K, pantothenic acid and derivatives thereof, biotin, panthenol, coenzyme $Q_{10}$ and idebenone.

14. The cochleate according to claim 5, wherein the amino acid or peptide is one or more selected from the group consisting of cysteine, methionine, serine, lysine, tryptophan, amino acid extract, epidermal growth factor (EGF), insulin-like growth factor (IGF), fibroblast growth factor (FGF), copper tripeptide-1, tripeptide-29, tripeptide-1, acetyl hexapeptide-8, nicotinoyl tripeptide-35, hexapeptide-12, hexapeptide-9, palmitoyl pentapeptide-4, palmitoyl tetrapeptide-7, palmitoyl tripeptide-29, palmitoyl tripeptide-1, nonapeptide-7, tripeptide-10 citrulline, sh-polypeptide-15, palmitoyl tripeptide-5, diaminopropionoyl tripeptide-33 and r-spider polypeptide-1.

15. The cochleate according to claim 5, wherein the anti-inflammatory agent is one or more selected from the group consisting of beta-glycyrrhetinic acid, glycyrrhetinic acid derivative, aminocaproic acid, hydrocortisone, β-glucan and licorice.

16. The cochleate according to claim 5, wherein the acne therapeutic agent is one or more selected from the group consisting of estradiol, estrogen, ethinyl estradiol, triclosan and azelaic acid.

17. The cochleate according to claim 5, wherein the microbicide is one or more selected from the group consisting of benzalkonium chloride, benzethonium chloride and halocalban.

18. The cochleate according to claim 5, wherein the female hormone is one or more selected from the group consisting of estradiol, ethinyl estradiol and isoflavone.

19. The cochleate according to claim 5, wherein the keratolytic agent is one or more selected from the group consisting of sulfur, salicylic acid, alpha-hydroxy acid (AHA), beta-hydroxy acid (BHA), and resorcin.

20. The cochleate according to claim 5, wherein the natural product is one or more selected from the group consisting of an extract of Japanese witch-hazel, an extract of *Lamium album* var. *barbatum*, an extract of *Hedyotis diffusa*, an extract of *Rheum palmatum*, an extract of licorice, an extract of aloe, an extract of chamomile, an extract of rose hip, an extract of horse chestnut, an extract of *ginseng*, an extract of *Luffa aegyptiaca*, an extract of cucumber, an extract of laver, an extract of sea mustard, an extract of *Dioscorea batatas*, an extract of snail, an extract of fruit of *Dioscorea polystachya*, hinokitiol and beta-carotene.

\* \* \* \* \*